(12) United States Patent
Sirard et al.

(10) Patent No.: US 10,736,937 B2
(45) Date of Patent: Aug. 11, 2020

(54) METHODS AND PHARMACEUTICAL COMPOSITIONS FOR THE TREATMENT OF BACTERIAL SUPERINFECTIONS POST-INFLUENZA

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ DE DROIT ET DE LA SANTÉ DE LILLE 2, Lille (FR); UNIVERSITÉ DE LILLE 1 SCIENCES ET TECHNOLOGIES, Villeneuve d'Ascq (FR); INSTITUT PASTEUR DE LILLE, Lille (FR)

(72) Inventors: Jean-Claude Sirard, Lille (FR); Christophe Carnoy, Lille (FR); François Trottein, Lille (FR); Rémi Porte, Lille (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ DE LILLE, Lille (FR); INSTITUT PASTEUR DE LILLE, Lille (FR)

( * ) Notice: Subject to any disclaimer, the term of this patent is extended or adjusted under 35 U.S.C. 154(b) by 169 days.

(21) Appl. No.: 15/537,596

(22) PCT Filed: Dec. 22, 2015

(86) PCT No.: PCT/EP2015/080924
§ 371 (c)(1),
(2) Date: Jun. 19, 2017

(87) PCT Pub. No.: WO2016/102536
PCT Pub. Date: Jun. 30, 2016

(65) Prior Publication Data
US 2018/0264077 A1 Sep. 20, 2018

(30) Foreign Application Priority Data
Dec. 23, 2014 (EP) .................................. 14307154

(51) Int. Cl.
| | | |
|---|---|---|
| *A61K 31/04* | (2006.01) | |
| *A61K 38/16* | (2006.01) | |
| *A61P 31/04* | (2006.01) | |
| *A61K 45/06* | (2006.01) | |

(52) U.S. Cl.
CPC ............ *A61K 38/164* (2013.01); *A61K 45/06* (2013.01); *A61P 31/04* (2018.01)

(58) Field of Classification Search
CPC ........ A61K 38/164; A61K 45/06; A61P 31/04
See application file for complete search history.

(56) References Cited

U.S. PATENT DOCUMENTS

| | | | |
|---|---|---|---|
| 9,906,747 B2 * | 2/2018 | Araoka | ................. H04N 5/378 |
| 2011/0110962 A1 * | 5/2011 | Sirard | .................... A61K 39/39 |
| | | | 424/184.1 |

FOREIGN PATENT DOCUMENTS

| | | |
|---|---|---|
| WO | 2009/156405 A1 | 12/2009 |
| WO | 2011/161491 A1 | 12/2011 |
| WO | 2014/053481 A1 | 4/2014 |
| WO | 2014/053482 A1 | 4/2014 |

OTHER PUBLICATIONS

Abgueguen et al (Antimicrobial Agents and Chemotherapy, Jan. 2007, p. 208-214 (Year: 2007).*
Muñoz Natalia et al: "Mucosal administration of flagellin protects mice from *Streptococcus pneumoniae* lung infection", Infection and Immunity, American Society for Mucrobiology, US, vol. 78. No. 10, Oct. 1, 2010, pp. 4226-4233.

* cited by examiner

Primary Examiner — Sudhakar Katakam
(74) Attorney, Agent, or Firm — W&C IP

(57) ABSTRACT

The present invention relates to methods and pharmaceutical compositions for the treatment of bacterial superinfections post-influenza. In particular, the present invention relates to a method of treating a bacterial superinfection post-influenza in a subject in need thereof comprising administering the subject with a therapeutically effective amount of a flagellin polypeptide optionally in combination with at least one antibiotic.

Figure 2:
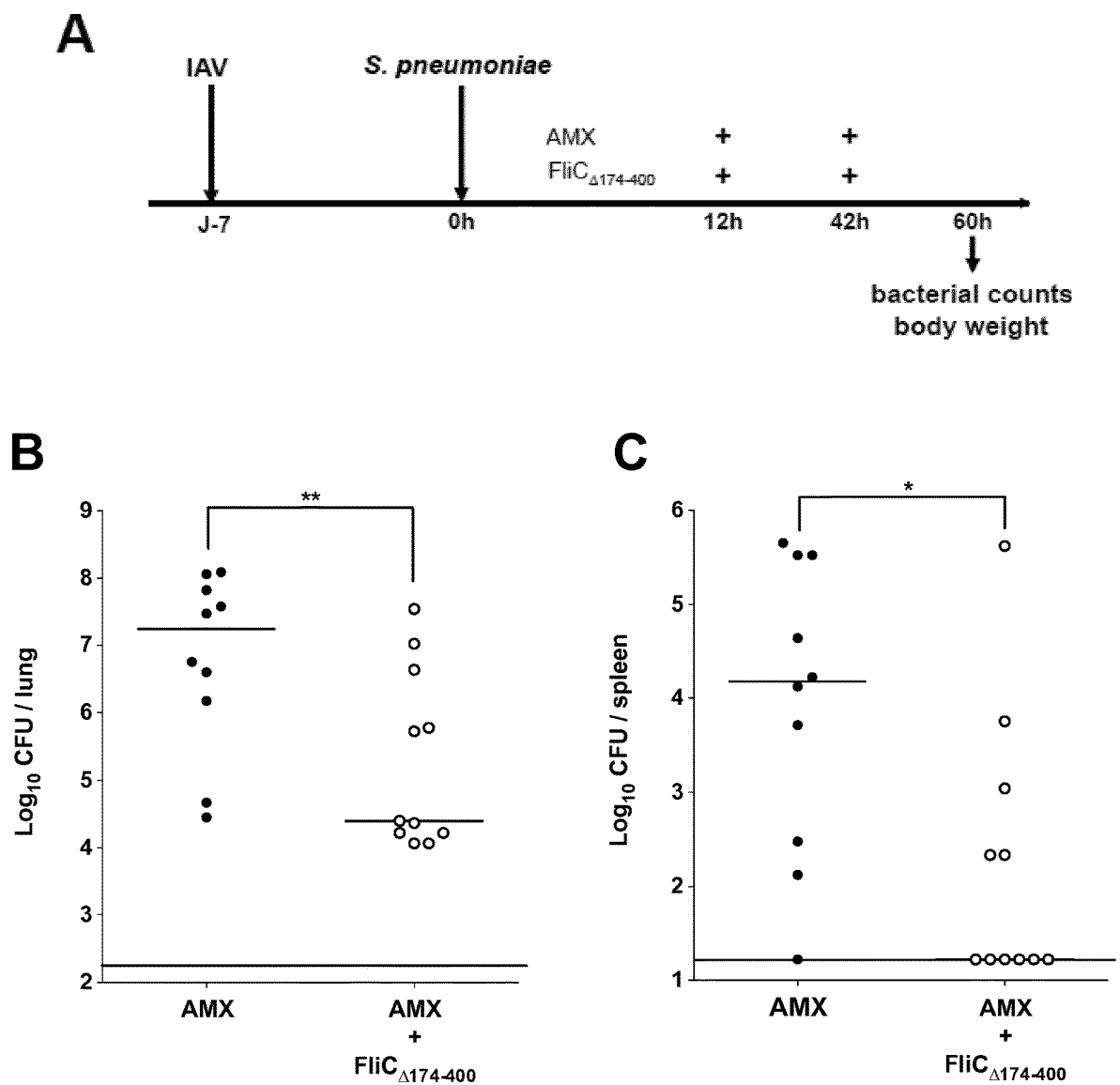

16 Claims, 3 Drawing Sheets
Specification includes a Sequence Listing.

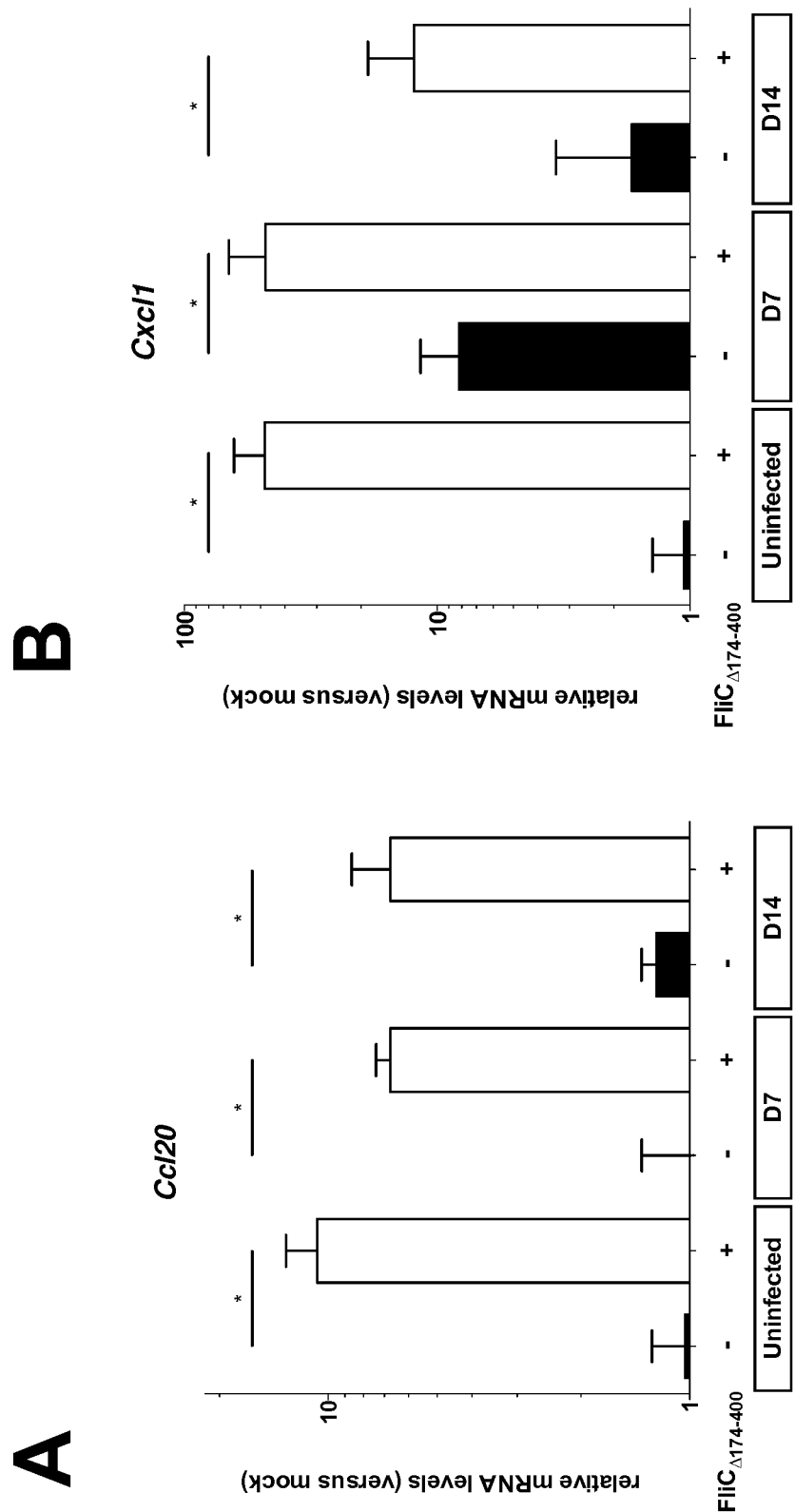
Figure 1 A&B

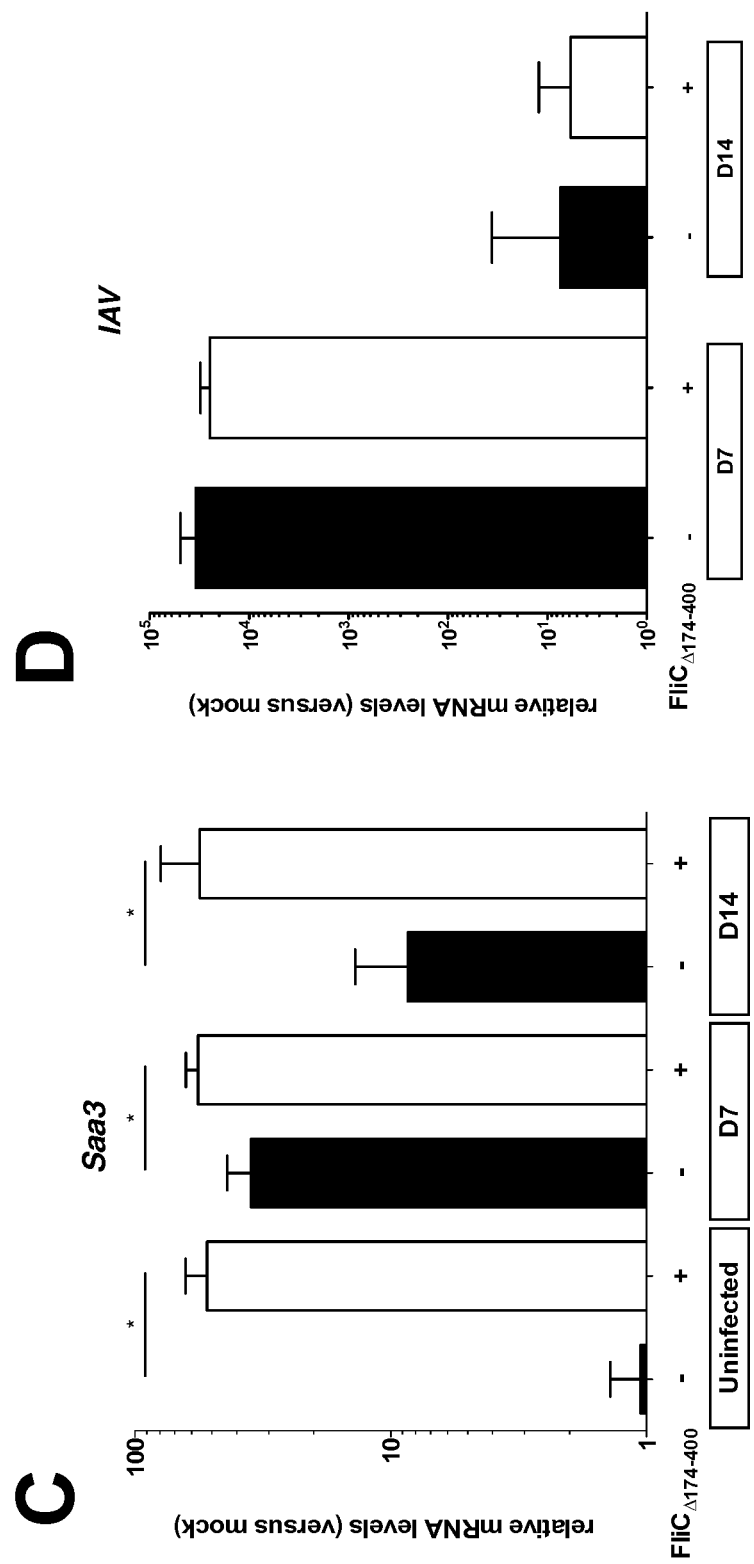
Figure 1 C&D

SEQUENCE LISTING

<160> NUMBER OF SEQ ID NOS: 4

<210> SEQ ID NO 1
<211> LENGTH: 585
<212> TYPE: PRT
<213> ORGANISM: Escherichia coli

<400> SEQUENCE: 1

Met Ala Gln Val Ile Asn Thr Asn Ser Leu Ser Leu Ile Thr Gln Asn

```
1               5                    10                   15
Asn Ile Asn Lys Asn Gln Ser Ala Leu Ser Ser Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
50                      55                  60

Ala Arg Asn Ala Asn Asp Gly Ile Ser Val Ala Gln Thr Thr Glu Gly
65                  70                  75                  80

Ala Leu Ser Glu Ile Asn Asn Leu Gln Arg Ile Arg Glu Leu Thr
                85                  90                  95

Val Gln Ala Thr Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
            115                 120                 125

Gln Thr Gln Phe Asn Gly Val Asn Val Leu Ala Lys Asp Gly Ser Met
            130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Gly Leu Asn Gly Phe Asn Val Asn
                165                 170                 175

Gly Lys Gly Thr Ile Thr Asn Lys Ala Ala Thr Val Ser Asp Leu Thr
            180                 185                 190

Ser Ala Gly Ala Lys Leu Asn Thr Thr Thr Gly Leu Tyr Asp Leu Lys
            195                 200                 205

Thr Glu Asn Thr Leu Leu Thr Thr Asp Ala Ala Phe Asp Lys Leu Gly
            210                 215                 220

Asn Gly Asp Lys Val Thr Val Gly Gly Val Asp Tyr Thr Tyr Asn Ala
225                 230                 235                 240

Lys Ser Gly Asp Phe Thr Thr Lys Ser Thr Ala Gly Thr Gly Val
                245                 250                 255

Asp Ala Ala Ala Gln Ala Ala Asp Ser Ala Ser Lys Arg Asp Ala Leu
                260                 265                 270

Ala Ala Thr Leu His Ala Asp Val Gly Lys Ser Val Asn Gly Ser Tyr
            275                 280                 285

Thr Thr Lys Asp Gly Thr Val Ser Phe Glu Thr Asp Ser Ala Gly Asn
            290                 295                 300

Ile Thr Ile Gly Gly Ser Gln Ala Tyr Val Asp Asp Ala Gly Asn Leu
305                 310                 315                 320

Thr Thr Asn Asn Ala Gly Ser Ala Ala Lys Ala Asp Met Lys Ala Leu
                325                 330                 335

Leu Lys Ala Ala Ser Glu Gly Ser Asp Gly Ala Ser Leu Thr Phe Asn
            340                 345                 350

Gly Thr Glu Tyr Thr Ile Ala Lys Ala Thr Pro Ala Thr Thr Pro
            355                 360                 365

Val Ala Pro Leu Ile Pro Gly Gly Ile Thr Tyr Gln Ala Thr Val Ser
            370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
                405                 410                 415

Gly Glu Ser Ser Asp Ala Ala Lys Ser Tyr Val Asp Asp Lys Gly Gly
            420                 425                 430
```

Ile Thr Asn Val Ala Asp Tyr Thr Val Ser Tyr Ser Val Asn Lys Asp
            435                 440                 445

Asn Gly Ser Val Thr Val Ala Gly Tyr Ala Ser Ala Thr Asp Thr Asn
        450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
                485                 490                 495

Pro Leu Ala Ala Leu Asp Asp Ala Ile Ser Ser Ile Asp Lys Phe Arg
                500                 505                 510

Ser Ser Leu Gly Ala Ile Gln Asn Arg Leu Asp Ser Ala Val Thr Asn
                515                 520                 525

Leu Asn Asn Thr Thr Thr Asn Leu Ser Glu Ala Gln Ser Arg Ile Gln
            530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
                580                 585

<210> SEQ ID NO 2
<211> LENGTH: 495
<212> TYPE: PRT
<213> ORGANISM: Salmonella typhimurium

<400> SEQUENCE: 2

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp

```
            210                 215                 220
Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
            275                 280                 285

Leu Thr Glu Ala Lys Ala Ala Leu Thr Ala Ala Gly Val Thr Gly Thr
        290                 295                 300

Ala Ser Val Val Lys Met Ser Tyr Thr Asp Asn Gly Lys Thr Ile
305                 310                 315                 320

Asp Gly Gly Leu Ala Val Lys Val Gly Asp Tyr Tyr Ser Ala Thr
                325                 330                 335

Gln Asn Lys Asp Gly Ser Ile Ser Ile Asn Thr Thr Lys Tyr Thr Ala
                340                 345                 350

Asp Asp Gly Thr Ser Lys Thr Ala Leu Asn Lys Leu Gly Gly Ala Asp
            355                 360                 365

Gly Lys Thr Glu Val Val Ser Ile Gly Gly Lys Thr Tyr Ala Ala Ser
        370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 3
<211> LENGTH: 494
<212> TYPE: PRT
<213> ORGANISM: Salmonella typhimurium

<400> SEQUENCE: 3

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95
```

Gln Ser Ala Asn Ser Thr Asn Ser Gln Ser Asp Leu Asp Ser Ile Gln
              100                 105                 110

Ala Glu Ile Thr Gln Arg Leu Asn Glu Ile Asp Arg Val Ser Gly Gln
        115                 120                 125

Thr Gln Phe Asn Gly Val Lys Val Leu Ala Gln Asp Asn Thr Leu Thr
    130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Val Gln Gln
                165                 170                 175

Lys Tyr Lys Val Ser Asp Thr Ala Ala Thr Val Thr Gly Tyr Ala Asp
            180                 185                 190

Thr Thr Ile Ala Leu Asp Asn Ser Thr Phe Lys Ala Ser Ala Thr Gly
        195                 200                 205

Leu Gly Gly Thr Asp Gln Lys Ile Asp Gly Asp Leu Lys Phe Asp Asp
    210                 215                 220

Thr Thr Gly Lys Tyr Tyr Ala Lys Val Thr Val Thr Gly Gly Thr Gly
225                 230                 235                 240

Lys Asp Gly Tyr Tyr Glu Val Ser Val Asp Lys Thr Asn Gly Glu Val
                245                 250                 255

Thr Leu Ala Gly Gly Ala Thr Ser Pro Leu Thr Gly Gly Leu Pro Ala
            260                 265                 270

Thr Ala Thr Glu Asp Val Lys Asn Val Gln Val Ala Asn Ala Asp Leu
        275                 280                 285

Thr Glu Ala Lys Ala Ala Leu Thr Ala Ala Gly Val Thr Gly Thr Ala
    290                 295                 300

Ser Val Val Lys Met Ser Tyr Thr Asp Asn Asn Gly Lys Thr Ile Asp
305                 310                 315                 320

Gly Gly Leu Ala Val Lys Val Gly Asp Asp Tyr Tyr Ser Ala Thr Gln
                325                 330                 335

Asn Lys Asp Gly Ser Ile Ser Ile Asn Thr Thr Lys Tyr Thr Ala Asp
            340                 345                 350

Asp Gly Thr Ser Lys Thr Ala Leu Asn Lys Leu Gly Gly Ala Asp Gly
        355                 360                 365

Lys Thr Glu Val Val Ser Ile Gly Gly Lys Thr Tyr Ala Ala Ser Lys
    370                 375                 380

Ala Glu Gly His Asn Phe Lys Ala Gln Pro Asp Leu Ala Glu Ala Ala
385                 390                 395                 400

Ala Thr Thr Thr Glu Asn Pro Leu Gln Lys Ile Asp Ala Ala Leu Ala
                405                 410                 415

Gln Val Asp Thr Leu Arg Ser Asp Leu Gly Ala Val Gln Asn Arg Phe
            420                 425                 430

Asn Ser Ala Ile Thr Asn Leu Gly Asn Thr Val Asn Asn Leu Thr Ser
        435                 440                 445

Ala Arg Ser Arg Ile Glu Asp Ser Asp Tyr Ala Thr Glu Val Ser Asn
    450                 455                 460

Met Ser Arg Ala Gln Ile Leu Gln Gln Ala Gly Thr Ser Val Leu Ala
465                 470                 475                 480

Gln Ala Asn Gln Val Pro Gln Asn Val Leu Ser Leu Leu Arg
                485                 490

<210> SEQ ID NO 4
<211> LENGTH: 4
<212> TYPE: PRT

```
<213> ORGANISM: Artificial
<220> FEATURE:
<223> OTHER INFORMATION: Synthetic peptide linker

<400> SEQUENCE: 4

Gly Ala Ala Gly
1
```

METHODS AND PHARMACEUTICAL COMPOSITIONS FOR THE TREATMENT OF BACTERIAL SUPERINFECTIONS POST-INFLUENZA

FIELD OF THE INVENTION

The present invention relates to methods and pharmaceutical compositions for the treatment of bacterial superinfections post-influenza.

BACKGROUND OF THE INVENTION

Influenza A virus (IAV) infection is one of the most important causes of respiratory tract diseases and is responsible for widespread morbidity and mortality. During the first several days after infection, the host develops a complex and effective innate immune response that allows to contain IAV replication pending the development of adaptive immune responses. However, at later time points, increased susceptibility to bacterial superinfection can occur leading to mortality during IAV epidemics and pandemics. For instance bacterial pneumonias accounted for the majority of deaths (~50 million deaths worldwide) in the 1918 pandemic (Spanish flu). Among the predominant bacteria species causing bacterial superinfection post-IAV are *Streptococcus pneumoniae* (the pneumococcus), *Haemophilus influenzae* and *Staphylococcus aureus*. Thus, there is a need for treatment of bacterial superinfections post-influenza. Although there are evidences of specific features of individual types of bacteria, the mechanisms leading to enhance susceptibility to secondary bacterial infection seem to be broad-based and include alterations of mechanical and immunological defences. Indeed, alteration of the physical barriers to bacterial adhesion and invasion including alteration of the mucosa as well as the exposition of new attachment sites for the bacteria have been described. In parallel, impairment of the host innate (rather than adaptive) response is a cardinal feature of bacterial-associated pneumonia post-influenza challenge. There are now strong evidences that TLR5 signaling induces protective mechanisms against bacterial infections. For instance, it was also showed that mucosal administration of flagellin into mice could protect against *Streptococcus pneumoniae* lung infection. The anti-infectious properties of flagellin were mainly observed when the TLR5 ligand was co-administrated with the pathogen or 2 to 24 h before the bacterial challenge (Munoz N, Van Maele L, Marques J M, Rial A, Sirard J C, Chabalgoity J A. Mucosal administration of flagellin protects mice from *Streptococcus pneumoniae* lung infection. Infect Immun 2010; 78:4226-33).

SUMMARY OF THE INVENTION

The present invention relates to methods and pharmaceutical compositions for the treatment of bacterial superinfections post-influenza. In particular, the present invention is defined by the claims.

DETAILED DESCRIPTION OF THE INVENTION

The inventors investigated the effectiveness of a combination therapy consisting of flagellin+antibiotic on IAV-infected animals. For this purpose, animals infected with IAV for 7 days were infected with *S. pneumoniae* and treated with AMX and flagellin. They show that the combination therapy was highly effective to increase the therapeutic index of AMX both in lungs and spleen.

The present invention relates to a method of treating a bacterial superinfection post-influenza in a subject in need thereof comprising administering the subject with a therapeutically effective amount of a flagellin polypeptide optionally in combination with at least one antibiotic.

The subject can be human or any other animal (e.g., birds and mammals) susceptible to influenza infection (e.g. domestic animals such as cats and dogs; livestock and farm animals such as horses, cows, pigs, chickens, etc.). Typically said subject is a mammal including a non-primate (e.g., a camel, donkey, zebra, cow, pig, horse, goat, sheep, cat, dog, rat, and mouse) and a primate (e.g., a monkey, chimpanzee, and a human). In some embodiments, the subject is a human.

According to the invention the subject suffers or has suffered from an influenza infection. As used herein, the term "influenza infection" has its general meaning in the art and refers to the disease caused by an infection with an influenza virus. In some embodiments of the invention, influenza infection is associated with Influenza virus A or B. In some embodiments of the invention, influenza infection is associated with Influenza virus A. In some specific embodiments of the invention, influenza infection is cause by influenza virus A that is H1N1, H2N2, H3N2 or H5N1.

As used herein, the term "bacterial superinfection post-influenza" has its general meaning in the art and refers to a bacterial infection (e.g. bacterial pneumonia) which occurs in a subject who suffers or has suffered from an influenza infection. Typically, the bacterial superinfection occurs within 4, 5, 6, 7, 8, 9, 10, 11, 12, 13, 14, 15, 16, 17, 18, 19, 20, 21, 22, 23, 24, or 25 days after influenza infection. The method of the present invention is particularly suitable for the treatment of a bacterial superinfection post-influenza such as, but not limited to infections of the lower respiratory tract (e.g., pneumonia), middle ear infections (e.g., otitis media) and bacterial sinusitis. The bacterial superinfection may be caused by numerous bacterial pathogens. For example, they may be mediated by at least one organism selected from the group consisting of: *Streptococcus pneumoniae*; *Staphylococcus aureus*; *Haemophilus influenza*, *Myoplasma* species and *Moraxella catarrhalis*.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The method of the present invention is particularly suitable for subjects who are identified as at high risk for developing a bacterial superinfection post-influenza, including subjects who are at least 50 years old, subjects who reside in chronic care facilities, subjects who have chronic disorders of the pulmonary or cardiovascular system, subjects who required regular medical follow-up or hospitalization during the preceding year because of chronic metabolic diseases (including diabetes mellitus), renal dysfunction, hemoglobinopathies, or immunosuppression (including immunosuppression caused by medications or by human immunodeficiency [HIV] virus); children less than 14 years of age, patients between 6 months and 18 years of age who are receiving long-term aspirin therapy, and women who will be in the second or third trimester of pregnancy during the influenza season. More specifically, it is contemplated that the method of the invention is suitable for the treatment of bacterial superinfection post-influenza in subjects older than 1 year old and less than 14 years old (i.e., children); subjects between the ages of 50 and 65, and adults who are older than 65 years of age.

As used herein, the term "flagellin" has its general meaning in the art and refers to the flagellin contained in a variety of Gram-positive or Gram-negative bacterial species. Non-limiting sources of flagellins include but are not limited to *Escherichia*, e.g., *E. coli, Enterobacter, Erwinia, Klebsiella, Proteus, Salmonella*, e.g., *Salmonella enterica* serovar *Typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting. The amino acid sequences and nucleotide sequences of flagellins are publically available in the NCBI Genbank, see for example Accession Nos. AAL20871, NP_310689, BAB58984, AAO85383, AAA27090, NP_461698, AAK58560, YP_001217666, YP_002151351, YP_001250079, AAA99807, CAL35450, AAN74969, and BAC44986. The flagellin sequences from these and other species are intended to be encompassed by the term flagellin as used herein. Therefore, the sequence differences between species are included within the meaning of the term.

The term "flagellin polypeptide" is intended to a flagellin or a fragment thereof that retains the ability to bind and activate TLR5. As used herein the term "toll-like receptor 5" or "TLR5" has its general meaning in the art and is intended to mean a toll-like receptor 5 of any species, but preferably a human toll-like receptor 5. Upon activation, a TLR5 induces a cellular response by transducing an intracellular signal that is propagated through a series of signaling molecules from the cell surface to the nucleus. Typically, the intracellular domain of TLR5 recruits the adaptor protein, MyD88, which recruits the serine/threonine kinases IRAK (IRAK-1 and IRAK-4). IRAKs form a complex with TRAF6, which then interacts with various molecules that participate in transducing the TLR signal. These molecules and other TLR5 signal transduction pathway components stimulate the activity of transcription factors, such as fos, jun and NF-kB, and the corresponding induction of gene products of fos-, jun- and NF-kB-regulated genes, such as, for example, IL-6, TNF-alpha, CXCL1, CXCL2 and CCL20. Typically, the flagellin polypeptide of the present invention comprises the domains of flagellin involved in TLR5 signaling. The term "domain of flagellin" includes naturally occurring domain of flagellin and function conservative variants thereof. "Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence identity between any two proteins of similar function may vary and may be, for example, from 70% to 99%. Thus a "function-conservative variant" also includes a polypeptide which has at least 70% amino acid identity with the native sequence of flagellin or fragment thereof. According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99, or 100% of identity with the second amino acid sequence. In the same manner a first amino acid sequence having at least 90% of identity with a second amino acid sequence means that the first sequence has 90; 91; 92; 93; 94; 95; 96; 97; 98; or 99, or 100% of identity with the second amino acid sequence. Amino acid sequence identity is preferably determined using a suitable sequence alignment algorithm and default parameters, such as BLAST P (Karlin and Altschul, 1990). The domains of flagellin that are involved in TLR5 signaling are well known in the art, see for example Smith et al. (2003) Nat. Immunol. 4: 1247-1253 (e.g., amino acids 78-129, 135-173 and 394-444 of *S. typhimurium* flagellin or homologs or modified forms thereof).

Examples of flagellin polypeptides include but are not limited to those described in U.S. Pat. Nos. 6,585,980; 6,130,082; 5,888,810; 5,618,533; and 4,886,748; U.S. Patent Publication No. US 2003/0044429 A1; and in the International Patent Application Publications n° WO 2008097016 and WO 2009156405 which are incorporated by reference. An exemplary *E. coli* O157:H7 flagellin is SEQD ID NO:1. An exemplary *S. typhimurium* flagellin is SEQ ID NO:2 or SEQ ID NO:3.

In some embodiments, amino acid sequences having at least 70% of identity with SEQ ID NO: 1 SEQ ID NO:2 or SEQ ID NO:3 can be used as flagellin polypeptides according to the invention. In some embodiments, amino acid sequences having at least 90% of identity with SEQ ID NO: 1 SEQ ID NO:2 or SEQ ID NO:3 can be used as flagellin polypeptides according to the invention. In some embodiments, amino acid sequences having at least 70% of identity with SEQ ID NO:3 can be used as flagellin polypeptides according to the invention provided that the residues 89-96 (i.e. the residues that are involved in TLR5 detection) are not mutated (i.e. not substituted or not deleted). In some embodiments, amino acid sequences having at least 90% of identity with SEQ ID NO: 1 SEQ ID NO:2 or SEQ ID NO:3 can be used as flagellin polypeptides according to the invention provided that the residues 89-96 (i.e. the residues that are involved in TLR5 detection) are not mutated (i.e. not substituted or not deleted).

In some embodiments, the present encompasses the use of the flagellin recombinant polypeptides described in the International Patent Application n° WO 2009156405 which is incorporated by reference in its entirely.

In some embodiments, the flagellin polypeptide of the present invention comprises: a) a N-terminal peptide having at least 90% amino acid identity with the amino acid sequence starting from the amino acid residue located at position 1 of SEQ ID NO:3 and ending at an amino acid residue selected from the group consisting of any one of the amino acid residues located at positions 99 to 173 of SEQ ID NO:3; and b) a C-terminal peptide having at least 90% amino acid identity with the amino acid sequence starting at an amino acid residue selected from the group consisting of any one of the amino acid residues located at positions 401 to 406 of SEQ ID NO:3 and ending at the amino acid residue located at position 494 of SEQ ID NO:3, wherein: the said N-terminal peptide is directly linked to the said C-terminal peptide, or the said N-terminal peptide and the said C-terminal peptide are indirectly linked, one to the other, through a spacer chain. In some embodiments, said N-terminal peptide is selected from the group consisting of the amino acid sequences 1-99, 1-137, 1-160 and 1-173 of SEQ ID NO:3. In some embodiments, said C-terminal peptide is selected from the group consisting of the amino acid sequences 401-494 and 406-494 of SEQ ID NO: 3. In some embodiments, said N-terminal and C-terminal peptides consist of the amino acid sequences 1-173 and 401-494 of SEQ ID NO: 3, respectively. In some embodiments, said N-terminal and C-terminal peptides consist of the amino acid sequences 1-160 and 406-494 of SEQ ID NO: 3, respectively. In some embodiments, said N-terminal and C-terminal peptides consist of the amino acid sequences 1-137 and 406-494 of SEQ ID NO: 3, respectively. In some embodiments, said N-terminal peptide and the said C-terminal peptide are indirectly linked, one to the other, through an intermediate spacer chain consisting of a NH2-Gly-Ala-Ala-Gly-COOH (SEQ ID NO: 4) peptide sequence. In some embodiments, the asparagine amino acid residue located at position 488 of SEQ ID NO: 3 is replaced by a serine. In some embodiments, the flagellin polypeptide as above described comprises an additional methionine residue at the N-terminal end.

The flagellin polypeptide of the present invention is produced by any method well known in the art. In some embodiments, the flagellin polypeptide of the present invention is typically recombinantly produced by recombinant cells that have been transfected with a nucleic acid that encodes its amino acid sequence and allows its effective production within the transfected cells. The nucleic acid sequence encoding the flagellin polypeptide of the invention, may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence if the sequence is to be secreted, an origin of replication, one or more marker genes, an enhancer element, a promoter, and a transcription termination sequence. Construction of suitable vectors containing one or more of these components employs standard ligation techniques that are known to the skilled artisan. Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An example of suitable selectable markers for mammalian cells are those that enable the identification of cells competent to take up the nucleic acid encoding the flagellin polypeptide of the invention such as DHFR or thymidine kinase. An appropriate host cell when wild-type DHFR is employed is the CHO cell line deficient in DHFR activity. Expression and cloning vectors usually contain a promoter operably linked to the nucleic acid sequence encoding the flagellin polypeptide to direct mRNA synthesis. Promoters recognized by a variety of potential host cells are well known. Promoters suitable for use with prokaryotic hosts include the beta-lactamase and lactose promoter systems, alkaline phosphatase, a tryptophan (trp) promoter system, and hybrid promoters such as the tac promoter. Promoters for use in bacterial systems also will contain a Shine-Dalgarno (S. D.) sequence operably linked to the DNA encoding the flagellin polypeptide of the invention. Host cells are transfected or transformed with expression or cloning vectors described herein for flagellin polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991). Suitable host cells for cloning or expressing the DNA in the vectors herein include prokaryote, yeast, or higher eukaryote cells. Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31, 446); *E. coli* X1776 (ATCC 31,537); *E. coli* strain W3110 (ATCC 27,325); and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published 12 Apr. 1989), *Pseudomonas* such as *P. aeruginosa*, and *Streptomyces*. These examples are illustrative rather than limiting. Strain SIN41 of *Salmonella typhimurium* (fliC fljB), is particularly interesting for the production of flagellin polypeptides of the invention, since these prokaryotic host cells do not secrete any flagellins (Proc Natl Acad Sci USA. 2001; 98:13722-7). However flagellins are secreted through specialized secretion system: the so called "Type III secretion system". Interestingly, strain SIN41 produces all components of the type III secretion system required for optimal flagellin secretion. Cloning sequence coding new flagellin peptides under fliC promoter enables secretion in large amounts of the flagellin polypeptides of interest in strain SIN41. Strain W3110 is also interesting because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W31 10 strain 27C7 (ATCC 55,244), which has the complete genotype tonA ptr3 phoA E15 (argF-lac)169 degP ompT kan.sup.r; *E. coli* W31 10 strain 37D6, which has the complete genotype tona ptr3 phoA E15 (argF-lac)169 degP ompT rbs7 ilvG kan.sup.r; *E. coli* W31 10 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. The *E. coli* strains MG1655, MG1655 AfimA-H or MKS12, a fliD- and -f/m>A-/-/-deleted MG1655 strain are also interesting candidates for production of recombinant flagellins as secreted proteins (Nat Biotechnol. 2005; (4):475-81). Alternatively, in vitro methods of cloning, e.g., PCR or other nucleic acid polymerase reactions, are suitable. Flagellin polypeptide of the invention may be recovered from culture medium or from host cell lysates. If membrane-bound, it can be released from the membrane using a suitable detergent solution (e.g., TRITON-XTM. 100) or by enzymatic cleavage. In some embodiments, the flagellin polypeptide is purified from the supernatant of recombinant *S. Typhimurium* SIN41 (fliC fljB), as disclosed in Nempont et al. (Nempont, C. C., D.; Rumbo, M.; Bompard, C.; Villeret, V.; Sirard, J. C. 2008. Deletion of flagellin's hypervariable region abrogates antibody-mediated neutralization and systemic activation of TLR5-dependent immunity. J Immunol 181:2036-2043.). In particular, *Salmonella* were grown in Luria-Bertani (LB) broth for 6-18 hours at 37° C. with agitation. The supernatant was filtered and saturated with 60% ammonium sulfate (Sigma Aldrich, USA). The precipitated materials were recovered by centrifugation, solubilization in 20 mM Tris/HCl pH7.5 and then dialysis. The proteins were further purified by successive rounds of hydroxyapatite, anion exchange, and size exlusion chromatography (Bio-Rad Laboratories, USA; GE Healthcare, Sweden). Lastly, the proteins were depleted of lipopolysaccharide (LPS) using a polymyxin B column (Pierce, USA). Using the Limulus assay (Associates of Cape Cod Inc., USA), the residual LPS concentration was determined to be less than 30 pg LPS per µg recombinant flagellin. Constructs encoding the flagellins may be generated by PCR and cloned into the expression vector pET22b+. The plasmids can be introduced in *Escherichia coli* BL21 (DE3) and protein production can be induced by adding IPTG 1 mM. After disruption on French press, the soluble fraction was depleted of lipopolysaccharide (LPS) using Triton X-114 extraction. If flagellins are found in the insoluble fraction after the French-press, inclusion bodies are denatured in presence of Urea 8M followed by dialysis and Triton X-114 extraction. The proteins can then be purified on anion exchange chromatography and gel filtration. Finally, proteins can be again depleted of LPS using a polymyxin B column (Pierce, USA).

In some embodiments, the antibiotic is selected from the group consisting of aminoglycosides, beta lactams, quinolones or fluoroquinolones, macrolides, sulfonamides, sulfamethaxozoles, tetracyclines, streptogramins, oxazolidinones (such as linezolid), rifamycins, glycopeptides, polymixins, lipo-peptide antibiotics.

Tetracyclines belong to a class that shares a four-membered ring structure composed of four fused 6-membered (hexacyclic) rings. The tetracyclines exhibit their activity by inhibiting the binding of the aminoacyl tRNA to the 30S ribosomal subunit in susceptible bacteria. Tetracyclines for use in the invention include chlortetracycline, demeclocycline, doxycycline, minocycline, oxytetracycline, chlortetracycline, methacycline, mecocycline, tigecycline, limecycline, and tetracycline. The tetracyclines are effective against many known organisms including a-hemolytic streptococci, nonhemolytic streptococci, gram negative bacilli, rickettsiae, spirochetes, *Mycoplasma*, and *Chlamydia*.

Aminoglycosides are compounds derived from species of *Streptomyces* or *Micomonospora* bacteria and are primarily used to treat infections caused by gram-negative bacteria. Drugs belonging to this class all possess the same basic chemical structure, i.e., a central hexose or diaminohexose molecule to which two or more amino sugars are attached by a glycosidic bond. The aminoglycosides are bactericidal antibiotics that bind to the 30S ribosome and inhibit bacterial protein synthesis. They are active primarily against aerobic gram-negative bacilli and staphylococci. Aminoglycoside antibiotics for use in the invention include amikacin (Amikin®), gentamicin (Garamycin®), kanamycin (Kantrex®), neomycin (Mycifradin®), netilmicin (Netromycin®), paromomycin (Humatin®), streptomycin, and tobramycin (TOBI Solution®, TobraDex®).

Macrolides are a group of polyketide antibiotic drugs whose activity stems from the presence of a macrolide ring (a large 14-, 15-, or 16-membered lactone ring) to which one or more deoxy sugars, usually cladinose and desosamine, are attached. Macrolides are primarily bacteriostatic and bind to the 50S subunit of the ribosome, thereby inhibiting bacterial synthesis. Macrolides are active against aerobic and anaerobic gram positive cocci (with the exception of enterococci) and against gram-negative anaerobes. Macrolides for use in the invention include azithromycin (Zithromax®), clarithromycin (Biaxin®), dirithromycin (Dynabac®), erythromycin, clindamycin, josamycin, roxithromycin and lincomycin.

Ketolides belong to a class of semi-synthetic 14-membered ring macrolides in which the erythromycin macrolactone ring structure and the D-desosamine sugar attached at position 5 are retained, however, replacing the L-cladinose5 moiety and hydroxyl group at position 3 is a3-keto functional group. The ketolides bind to the 23S rRNA, and their mechanism of action is similar to that of macrolides (Zhanel, G. G., et al., Drugs, 2001; 61(4):443-98). The ketolides exhibit good activity against gram-positive aerobes and some gram-negative aerobes, and possess excellent activity against *Streptococcus* spp. including mefA and ermB-producing *Streptococcus pneumoniae*, and *Haemophilus influenzae*. Representative ketolides for use in the invention include telithromycin (formerly known as HMR-3647), HMR 3004, HMR 3647, cethromycin, EDP-420, and ABT-773.

Structurally, the quinolones possess a 1,4 dihydro-4-oxoquinolinyl moiety bearing an essential carboxyl group at position 3. Functionally, the quinolones inhibit prokaryotic type II topoisomerases, namely DNA gyrase and, in a few cases, topoisomerase IV, through direct binding to the bacterial chromosome. Quinolones for use in the invention span first, second, third and fourth generation quinolones, including fluoroquinolones. Such compounds include nalidixic acid, cinoxacin, oxolinic acid, flumequine, pipemidic acid, rosoxacin, norfloxacin, lomefloxacin, ofloxacin, enrofloxacin, ciprofloxacin, enoxacin, amifloxacin, fleroxacin, gatifloxacin, gemifloxacin, clinafloxacin, sitafloxacin, pefloxacin, rufloxacin, sparfloxacin, temafloxacin, tosufloxacin, grepafloxacin, levofloxacin, moxifloxacin, and trovafloxacin. Additional quinolones suitable for use in the invention include those described in Hooper, D., and Rubinstein, E., "Quinolone Antimicrobial Agents, Vd Edition", American Society of Microbiology Press, Washington D.C. (2004).

Drugs belonging to the sulfonamide class all possess a sulfonamide moiety, SO2NH2, or a substituted sulfonamide moiety, where one 15 of the hydrogens on the nitrogen is replaced by an organic substituent. Illustrative N-substituents include substituted or unsubstituted thiazole, pyrimidine, isoxazole, and other functional groups. Sulfonamide antibiotics all share a common structural feature, i.e., they are all benzene sulfonamides, 20 meaning that the sulfonamide functionality is directly attached to a benzene ring. The structure of sulfonamide antibiotics is similar to p-aminobenzoic acid (PABA), a compound that is needed in bacteria as a substrate for the enzyme, dihydropteroate synthetase, for the synthesis of tetrahydro-25 folic acid. The sulfonamides function as antibiotics by interfering with the metabolic processes in bacteria that require PABA, thereby inhibiting bacterial growth and activity. Sulfonamide antibiotics for use in the invention include the following: mafenide, phtalylsulfathiazole, succinylsulfathiazole, sulfacetamide, sulfadiazine, sulfadoxine, sulfamazone, sulfamethazine, sulfamethoxazole, sulfametopirazine, sulfametoxypiridazine, sulfametrol, sulfamonomethoxine, sulfamylon, sulfanilamide, sulfaquinoxaline, sulfasalazine, sulfathiazole, sulfisoxazole, sulfisoxazole diolamine, and sulfaguanidine.

All members of beta-lactams possess a beta-lactam ring and a carboxyl group, resulting in 55 similarities in both their pharmacokinetics and mechanism of action. The majority of clinically useful beta-lactams belong to either the penicillin group or the cephalosporin group, including cefamycins and oxacephems. The beta-lactams also include the carbapenems and monobactams. Generally speaking, beta-lactams inhibit bacterial cell wall synthesis. More specifically, these antibiotics cause 'nicks' in the peptidoglycan net of the cell wall that allow the bacterial protoplasm to flow from its protective net into the surrounding hypotonic medium. Fluid then accumulates in the naked 65 protoplast (a cell devoid of its wall), and it eventually bursts, leading to death of the organism. Mechanistically, beta-lactarns act by inhibiting D-alanyl-D-alanine transpeptidase activity by forming stable esters with the carboxyl of the open lactam ring attached to the hydroxyl group of the enzyme target site. Beta-lactams are extremely effective and typically are of low toxicity. As a group, these drugs are active against many gram-positive, gram-negative and anaerobic organisms. Drugs falling into this category include 2-(3-alanyl)clavam, 2-hydroxymethylclavam, 7-methoxycephalosporin, epithienamycin, acetyl-thienamycin, amoxicillin, apalcillin, aspoxicillin, azidocillin, azlocillin, aztreonam, bacampicillin, blapenem, carbenicillin, carfecillin, carindacillin, carpetimycin A and B, cefacetril, cefaclor, cefadroxil, cefalexin, cefaloglycin, cefaloridine, cefalotin, cefamandole, cefapirin, cefatrizine, cefazedone, cefazolin, cefbuperazone, cefcapene, cefdinir, cefditoren, cefepime, cefetamet, cefixime, cefinenoxime, cefinetazole, cefminox, cefmolexin, cefodizime, cefonicid, cefoperazone, ceforamide, cefoselis, cefotaxime, cefotetan, cefotiam, cefoxitin, cefozopran, cefpiramide, cefpirome, cefpodoxime, cefprozil, cefquinome, cefradine, cefroxadine, cefsulodin, ceftazidime, cefteram, ceftezole, ceftibuten, ceftizoxime, ceftriaxone, cefuroxime, cephalosporin C, cephamycin A, cephamycin C, cephalothin, chitinovorin A, chitinovorin B, chitinovorin C, ciclacillin, clometocillin, cloxacillin, cycloserine, deoxy pluracidomycin B and C, dicloxacillin, dihydro pluracidomycin C, epicillin, epithienamycin D, E, and F, ertapenem, faropenem, flomoxef, flucloxacillin, hetacillin, imipenem, lenampicillin, loracarbef, mecillinam, meropenem, metampicillin, meticillin (also referred to as methicillin), mezlocillin, moxalactam, nafcillin, northienamycin, oxacillin, panipenem, penamecillin, penicillin G, N, and V, phenethicillin, piperacillin, povampicillin, pivcefalexin, povmecillinam, pivmecillinam, pluracidomycin B, C, and D, propicillin, sarmoxicillin, sulbactam, sultamicillin, talampicillin, temocillin, terconazole, thienamycin, andticarcillin.

Over 400 natural antimicrobial peptides have been isolated and characterized. Based on chemical structure, these peptides may be classified into two main groups: linear and cyclic (R. E. Hancock et al, Adv. Microb. Physiol., 1995, 37: 135-137; H. Kleinkauf et al., Criti. Rev. Biotechnol., 198, 8: 1-32; D. Perlman and M. Bodansky, Annu. Rev. Biochem., 1971, 40: 449-464). The mode of action for the majority of these peptides (both linear and cyclic) is believed to involve membrane disruption, leading to cell leakage (A. Mor, Drug Develop. Res., 2000, 50: 440-447). The linear peptides, such as magainins and melitting, exist mainly as a-helical amphipathic structures (containing segregated hydrophobic and hydrophilic moieties), or as β-helices as found in gramicidin A (GA). Cyclic peptides, which mainly adopt an amphipatic β-sheet structures can be further divided into two subgroups: those containing disulfide bonds, such as tachyplesin, and those that do not, such as gramicidin S (D. Audreu and L. Rivas, Biopolymers, 1998, 47: 415-433). Peptide antibiotics also fall into two classes: non-ribosomally synthesized peptides, such as the gramicicins, polymyxins, bacitracins, glycopeptides, etc., and ribosomally synthesized (natural) peptides. The former are often drastically modified and are largely produced by bacteria, whereas the latter are produced by all species of life (including bacteria) as a major component of the natural host defense molecules of these species. In certain embodiments, the peptide antibiotic is a lipopeptide antibiotic such as colistin, daptomycin, surfactin, friulimicin, aculeacin A, iturin A, and tsushimycin. Colistin (also called Colimycin) is a polymixin antibiotic discovered more than 50 years ago. It is a cyclic lipopeptide antibiotic which penetrates the cell wall of Gram negative bacteria by self-induced mechanism by chelating divalent ions. Colistin destabilizes the wall and can insinuate into it. Colistin basically perforates the cell wall, causing distortion of this structure and the release of intracellular constituents. Increasing multidrug resistance in Gram-negative bacteria, in particular *Pseudomonas aeruginosa*, *Acinetobacter baumannii*, and *Klebsiella pneumoniae*, presents a critical problem. Limited therapeutic options have forced infectious disease clinicians and microbiologists to reappraise the clinical application of Colistin. Colistin is associated with neurotoxicity and nephrotoxicity. Dosage regimen and novel formulation may be an answer to address the toxicity issue.

In some embodiments, the flagellin polypeptide is used in combination with amoxicillin.

In some embodiments, the flagellin polypeptide is used in combination with Bactrim® which contains both sulfamethoxazole and trimethoprime.

In some embodiments, the flagellin polypeptide and the antibiotic are to be used simultaneous or sequentially within a given time. The antibiotic can be applied in either order, e.g. the antibiotic can be applied first and then the flagellin polypeptide can be applied or vice versa. It is obvious that when a composition comprising both the antibiotic and flagellin polypeptide is used both components will be applied at the same time by the same routes or by different routes of administration. For example, the antibiotic may be administered to the subject via the oral route and the flagellin polypeptide is administered to the subject via the intravenous route or via the intranasal route.

By a "therapeutically effective amount" is meant a sufficient amount of the flagellin polypeptide and/or antibiotic for the treatment of a bacterial superinfection post influenza at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically the active ingredient of the present invention (i.e. the flagellin polypeptide and/or antibiotic) is combined with pharmaceutically acceptable excipients, and optionally sustained-release matrices, such as biodegradable polymers, to form pharmaceutical compositions. The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In the pharmaceutical compositions of the present invention, the active ingredients of the invention can be administered in a unit administration form, as a mixture with conventional pharmaceutical supports. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. In some embodiments, the pharmaceutical composition of the invention is administered topically (i.e. in the respiratory tract of the subject). Therefore, the compositions can be formulated in the form of a spray, aerosol, solution, emulsion, or other form well-known to one of skill in the art. If the method of the invention comprises intranasal administration of a composition, the composition can be formulated in an aerosol form, spray, mist or in the form of drops. In particular, the active ingredients for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

The invention will be further illustrated by the following figures and examples. However, these examples and figures should not be interpreted in any way as limiting the scope of the present invention.

FIGURES

FIG. 1: Flagelin stimulates proinflammatory gene expression during Influenza A virus infection. C57BL/6 mice were infected intranasally with Influenza A virus (30 PFU). Seven or 14 days after viral infection, mice were treated intranasally with 2.5 µg flagellin $FliC_{\Delta 174\text{-}400}$. Two hours post-flagellin stimulation, lungs were collected for analysis of transcript levels by quantitative PCR. Results are given as means±standard errors of the mean (n=4). (A-C) Messenger RNA levels are expressed relative to those of the mock group (uninfected and untreated), arbitrary set to 1. (D) Virus RNA are expressed compared to a housekeeping gene expression (Bactin) and the limit of detection was set arbitrary to 1 with an uninfected C57BL/6 mice. Statistical significance was determined with the non parametric test of Mann-Whitney (*: p<0.05).

FIG. 2: The $AMX/FliC_{\Delta 174\text{-}400}$ treatment protect Influenza A virus-S. pneumoniae co-infected mice. (A) C57BL/6 mice were infected with influenza A virus H3N2 (30 PFU). Seven days later, mice were infected with S. pneumoniae ($10^3$ CFU). Twelve hours and 42 h later, animals were treated intragastrically with 5 µg AMX and intranasally with 2.5 µg flagellin $FliC_{\Delta 174\text{-}400}$. At 60 h, bacterial counts in lung (B) and spleen (C) were determined by measuring CFU per tissue. Each dot represents CFU for an individual mouse. The solid line represents the threshold of detection. Statistical significance was determined with the non parametric test of Mann-Whitney (*: p<0.05 and **: p<0.01).

EXAMPLE

Materials & Methods
Bacterial Preparation
*Streptococcus pneumoniae* serotype 1 (clinical isolate E1586) was obtained from the National Reference Laboratory—Ministry of Health, Uruguay. Working stocks were prepared as follows: Todd Hewitt Yeast Broth (THYB) (Sigma-Aldrich—Saint-Louis, Mo.) was inoculated with fresh colonies grown in blood-agar plates, and incubated at 37° C. until OD600 nm of 0.7-0.9 units. Cultures were stored at −80° C. in THYB+glycerol 12% (vol/vol) up to 3 months. For mouse infection, working stocks were thawed and washed with sterile Dulbecco's Phosphate-Buffered Saline (DPBS; Gibco—Grand Island, N.Y.) and diluted to the appropriate concentration. Number of bacteria in stocks was confirmed by plating serial dilutions onto blood agar plates.

Mouse Model of Infection

Female BALB/c (6-8 weeks old) mice were obtained from Janvier laboratories (St. Berthevin, France). Animals were maintained in individually ventilated cages and handled in a vertical laminar flow cabinet (class II A2, ESCO—Hatboro, Pa.). All experiments complied with current national and institutional regulations and ethical guidelines (B59-350009—Institut Pasteur de Lille). Mice were anaesthetized by intraperitoneal (i.p.) injection of 1.25 mg ketamine (Imalgène, Merial—Lyon, France) plus 0.25 mg xylazine (Rompun, Bayer HealthCare—Loos, France) in 250 µl DPBS. Mice were infected i.n. with 50 µl of D-PBS containing 30 PFU of the highly-pathogenic murine adapted H3N2 Influenza A virus strain Scotland/20/74. Seven or 14 days post-viral challenge, mice were infected i.n. with 30 µl of D-PBS containing $10^3$ CFU of *S. pneumoniae*.

Flagellin and Antibiotic Administration

The constructs encoding the recombinant flagellins FliC$_{\Delta 174\text{-}400}$ (harboring a carboxy-terminal histidine Tag) and rFliC (harboring an amino-terminal histidine Tag) were generated by PCR and cloned into the expression vector pET22b+. The recombinant flagellins were produced as follows. The plasmids were introduced in *Escherichia coli* BL21(DE3) and protein production was induced by adding IPTG 1 mM. After disruption on French press, the soluble fraction was depleted of lipopolysaccharide (LPS) using Triton X-114 extraction as described previously. The proteins were purified successively on nickel affinity chromatography, anion exchange chromatography and gel filtration by Fast protein liquid chromatography (GE Healthcare). Finally, proteins were again depleted of LPS using a polymyxin B column (Pierce, USA). Using the Limulus assay (Associates of Cape Cod Inc., USA), the residual LPS concentration was determined to be less than 20 pg LPS per µg recombinant flagellin. Flagellins were heated for 10 min at 65° C. before use to ensure that proteins are mostly monomers. Flagellins in 30 µl DPBS were administrated i.n. under light anesthesia by inhalation of isoflurane (Axience—Pantin, France) using an anaesthesia non-rebreathing system (DRE-Compact 150, DRE Veterinary—Louisville, Ky.). Infected mice were treated by a suboptimal dose of amoxicillin (AMX) (5 µg in 200 µl water; amoxicillin VERTANAL™, Sigma-Aldrich—Saint-Louis, Mo.) intragastrically (i.g.) using a plastic tube feed (V0104030, ECIMED—Boissy-St-Léger, France). This represents a dose of AMX of 250 µg/kg for 6 to 8 week old mice.

Determination of Bacterial Load in Lungs and Spleen

Mice were sacrificed at different time points after infection by i.p. injection of 5.47 mg of sodium pentobarbital (CEVA Santé animale, Libourne, France) in 100 µl DPBS. Lungs and spleen were collected at selected time points after infection and homogenized with an UltraTurrax homogenizer (IKA-Werke, Staufen, Germany). Viable counts were determined by plating serial dilutions onto blood-agar plates.

Gene Expression Quantification by Real-Time RT-PCR

Total lung RNAs were extracted with the Nucleospin RNA II kit (Macherey Nagel—Hoerdt, France) and reverse-transcribed with the High-Capacity cDNA Archive Kit (Applied Biosystems—Foster city, Canada). The resulting cDNA was amplified using SYBR Green-based real-time PCR on a 7300 Real Time PCR System (Applied Biosystems). Primers specific for reference gene ActB, and chemokine-encoding genes Ccl20 and Cxcl1 were described previously [20]. Relative mRNA levels ($2^{-\Delta\Delta Ct}$) were determined by comparing first, the PCR cycle thresholds (Ct) for the gene of interest and Δctb (ΔCt) and second, the ΔCt values for treated and reference group (ΔΔCt), as described previously [20].

Statistical Analysis

Results are expressed as median±range. Statistical differences were analyzed using the Mann-Whitney test (GraphPad Prism 5.0) and were considered to be significant for p values<0.05.

Results:

We investigated the effectiveness of a combination therapy consisting of flagellin+antibiotic on IAV-infected animals. First, we defined whether flagellin is able to promote signaling in IAV-infected animals. We found that intranasal treatment with FliC$_{\Delta 174\text{-}400}$ was able to further increase the transcription of immune mediators in the context of IAV-infection both in the acute and resolution phases, e.g. 7 and 14 days post-infection (FIG. 1). We selected to assess the combination therapy in animals in acute infection. For this purpose, animals infected with IAV for 7 days were infected with *S. pneumoniae* and treated with AMX and flagellin (FIG. 2). Our data showed that the combination therapy was highly effective to increase the therapeutic index of AMX both in lungs and spleen.

REFERENCES

Throughout this application, various references describe the state of the art to which this invention pertains. The disclosures of these references are hereby incorporated by reference into the present disclosure.

The invention claimed is:

1. A method of treating a bacterial superinfection post-influenza in a subject in need thereof comprising
administering to the subject a therapeutically effective amount of a flagellin polypeptide,
wherein the bacterial superinfection occurs in a subject who has an influenza infection and/or within 4-25 days after influenza infection;
wherein:
the flagellin polypeptide retains the ability to bind and activate toll-like receptor 5 (TLR5),
the flagellin polypeptide is administered in combination with at least one antibiotic, and
the bacterial superinfection is mediated by *Streptococcus pneumoniae*.

2. The method of claim 1 wherein the subject is selected from the group consisting of subjects who are at least 50 years old, subjects who reside in chronic care facilities, subjects who have chronic disorders of the pulmonary or cardiovascular system, subjects who required regular medical follow-up or hospitalization during the preceding year because of chronic metabolic diseases, renal dysfunction, hemoglobinopathies, or immunosuppression, children less than 14 years of age, patients between 6 months and 18 years of age who are receiving long-term aspirin therapy, and women who will be in the second or third trimester of pregnancy during the influenza season.

3. The method of claim 1 wherein the flagellin polypeptide has at least 95% identity with SEQ ID NO:1, SEQ ID NO:2 or SEQ ID NO:3.

4. The method of claim 1 wherein the flagellin polypeptide comprises: a) a N-terminal peptide having at least 95% amino acid identity with the amino acid sequence starting from the amino acid residue located at position 1 of SEQ ID NO:3 and ending at an amino acid residue selected from the group consisting of any one of the amino acid residues located at positions 99 to 173 of SEQ ID NO:3; and b) a C-terminal peptide having at least 95% amino acid identity with the amino acid sequence starting at an amino acid residue selected from the group consisting of any one of the amino acid residues located at positions 401 to 406 of SEQ ID NO:3 and ending at the amino acid residue located at position 494 of SEQ ID NO:3, wherein: said N-terminal peptide is directly linked to said C-terminal peptide, or said N-terminal peptide and said C-terminal peptide are indirectly linked, one to the other, through a spacer chain.

5. The method of claim 4 wherein said N-terminal peptide is selected from the group consisting of the amino acid sequences 1-99, 1-137, 1-160 and 1-173 of SEQ ID NO:3.

6. The method of claim 4 wherein said C-terminal peptide is selected from the group consisting of the amino acid sequences 401-494 and 406-494 of SEQ ID NO:3.

7. The method of claim 4 wherein said N-terminal and C-terminal peptides consist of the amino acid sequences 1-173 and 401-494 of SEQ ID NO:3, respectively.

8. The method of claim 4 wherein said N-terminal and C-terminal peptides consist of the amino acid sequences 1-160 and 406-494 of SEQ ID NO:3, respectively.

9. The method of claim 4 wherein said N-terminal and C-terminal peptides consist of the amino acid sequences 1-137 and 406-494 of SEQ ID NO:3, respectively.

10. The method of claim 4 wherein said N-terminal peptide and said C-terminal peptide are indirectly linked, one to the other, through an intermediate spacer chain consisting of a NH2-Gly-Ala-Ala-Gly-COOH (SEQ ID NO:4) peptide sequence.

11. The method of claim 4 wherein the asparagine amino acid residue located at position 488 of SEQ ID NO:3 is replaced by a serine.

12. The method of claim 1, wherein the at least one antibiotic is selected from the group consisting of aminoglycosides, beta lactams, quinolones, or fluoroquinolones, macrolides, sulfonamides, sulfamethaxozoles, tetracyclines, streptogramins, and oxazolidinones, rifamycins, glycopeptides, polymixins, and lipo-peptide antibiotics.

13. The method of claim 1, wherein the at least one antibiotic is amoxicillin.

14. The method of claim 1, wherein the at least one antibiotic includes both sulfamethoxazole and trimethoprime.

15. The method of claim 1 wherein the flagellin polypeptide has at least 96, 97, 98 or 99% identity with SEQ ID NO:1, SEQ ID NO:2 or SEQ ID NO:3, with the caveat that residues 89-96 are not substituted or deleted.

16. The method of claim 1 wherein the flagellin polypeptide is SEQ ID NO:1, SEQ ID NO:2 or SEQ ID NO:3.

* * * * *